US00PP29301P3

(12) United States Plant Patent
Chartres

(10) Patent No.: US PP29,301 P3
(45) Date of Patent: May 22, 2018

(54) ***ACER PALMATUM* TREE NAMED 'CHACER01'**

(50) Latin Name: *Acer palmatum*
Varietal Denomination: CHACER01

(71) Applicant: Simon Chartres, Toolañgi (AU)

(72) Inventor: Simon Chartres, Toolañgi (AU)

( * ) Notice: Subject to any disclaimer, the term of this patent is extended or adjusted under 35 U.S.C. 154(b) by 15 days.

(21) Appl. No.: 14/999,706

(22) Filed: Jun. 15, 2016

(65) Prior Publication Data

US 2017/0367232 P1 Dec. 21, 2017

(51) Int. Cl.

| | |
|---|---|
| ***A01H 5/00*** | (2018.01) |
| ***A01H 5/04*** | (2018.01) |
| ***A01H 5/12*** | (2018.01) |

(52) U.S. Cl.
USPC ..... Plt./224
CPC ..... *A01H 5/04* (2013.01); *A01H 5/12* (2013.01)

(58) Field of Classification Search
USPC ..... Plt./224
See application file for complete search history.

*Primary Examiner* — Susan McCormick Ewoldt
(74) *Attorney, Agent, or Firm* — Cassandra Bright

(57) ABSTRACT

A new and distinct *Acer palmatum* tree named 'CHACER01' is disclosed, characterized by a unique stem arrangement giving the appearance of contortions by having branches with 30° to 45° bends at variable intervals. Plants are reasonably fast growing for a dwarf *Acer palmatum* with approximately 10 to 15 cm of growth per year with a maximum height of 1.2 meters. Fall color is orange/red autumn and leaf size of similar size and shape as the original common *Acer palmatum*. The new variety is a dwarf tree, typically used for outdoor garden or container use.

2 Drawing Sheets

Figure 1:
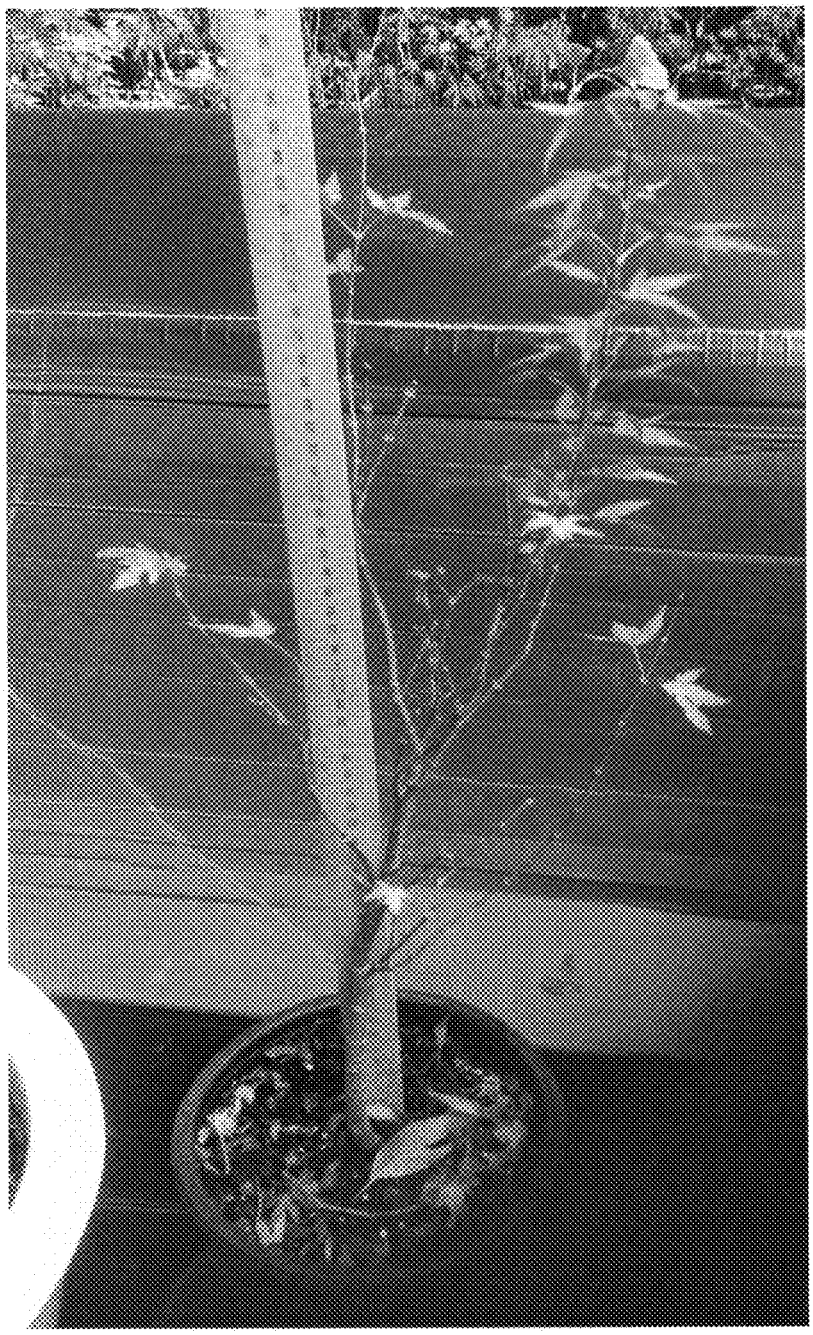

Latin name of the genus and species: *Acer palmatum.*
Variety denomination: 'CHACER01'.

BACKGROUND OF THE INVENTION

The new cultivar is a product of chance discovery. The new variety was discovered as a chance seedling emerging among a planting of various *Acer palmatum* trees. The inventor discovered this seedling in 1998 at a commercial nursery in Toolangi, Victoria, Australia.

Asexual reproduction of the new cultivar 'CHACER01' was first performed during 1998 at a commercial nursery in Toolangi, Victoria, Australia. This was conducted by the conventional commercial practice of grafting semi-softwood cuttings onto *Acer palmatum* seedling rootstock. Subsequent propagation has shown that the unique features of this cultivar are stable and have been reproduced true to type for five successive generations.

SUMMARY OF THE INVENTION

The cultivar 'CHACER01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CHACER01' grown in Toolangi, Australia. These characteristics in combination distinguish 'CHACER01' as a new and distinct *Acer palmatum* cultivar:

1. Variable stem arrangement giving the appearance of contortions by having branches with 30 to 45° bends at informal intervals.

2. Reasonably fast growing for a dwarf *Acer palmatum* tree with approximately 10 to 15 cm of growth per year to a maximum height of around 1.2 meters.
3. Orange/red Autumn coloration of the leaf.
4. Foliage of similar size and shape to common *Acer palmatum.*

PARENT COMPARISON

The breeder cannot confirm parent varieties, as several *Acer palmatum* varieties were present in the planting in which the new variety was discovered.

COMMERCIAL COMPARISON

Plants of the new cultivar 'CHACER01' are similar to plants of *Acer palmatum* 'Kamagata', unpatented, in most horticultural characteristics, however, plants of the new cultivar 'CHACER01' differ in the following;

1. The new variety has a variable and contorted stem arrangement, whereas this comparator has a uniform and straight stem arrangement.
2. The new variety has medium leaf lobe length, whereas 'Kamagata' has long leaf lobe length.

Plants of the new cultivar 'CHACER01' are similar to plants of the unpatented commercial variety, *Acer palmatum* 'Yatsubusa Kashima' in most horticultural characteristics, however, plants of the new cultivar 'CHACER01' differ in the following;

1. The new variety has a variable occurring and contorted stem arrangement, whereas this comparator has formal and straight stem arrangement.
2. The new variety has orange/red autumn foliage color, whereas 'Yatsubusa Kashima' has yellow/orange autumn foliage color.

3. The new variety has an overall height of 1.2 meters, whereas the parent has an overall height of 1.8 meters.

Plants of the new cultivar 'CHACER01' are similar to plants of the unpatented commercial variety *Acer palmatum* 'Mikawa Yatsubusa' in most horticultural characteristics. However, plants of the new cultivar differ in the following characteristics:

1. The new variety has a relatively medium to fast growth rate, whereas the comparator has a relatively slow growth rate.
2. The new variety has medium leaf size, whereas the comparator has a large leaf size.
3. The new variety has an overall plant height of 1.2 meters, whereas the comparator has an overall plant height of 1.8 meters.
4. While the new variety 'CHACER01' has short internode spacing the comparator has shorter internode spacing.

BRIEF DESCRIPTION OF THE PHOTOGRAPH

The accompanying photograph in FIG. 1 illustrates in full color a typical tree of 'CHACER01' grown outdoors, with some Fall coloration to the foliage. Age of the tree in FIG. 1 is approximately 3.5 years.

Figure 2:
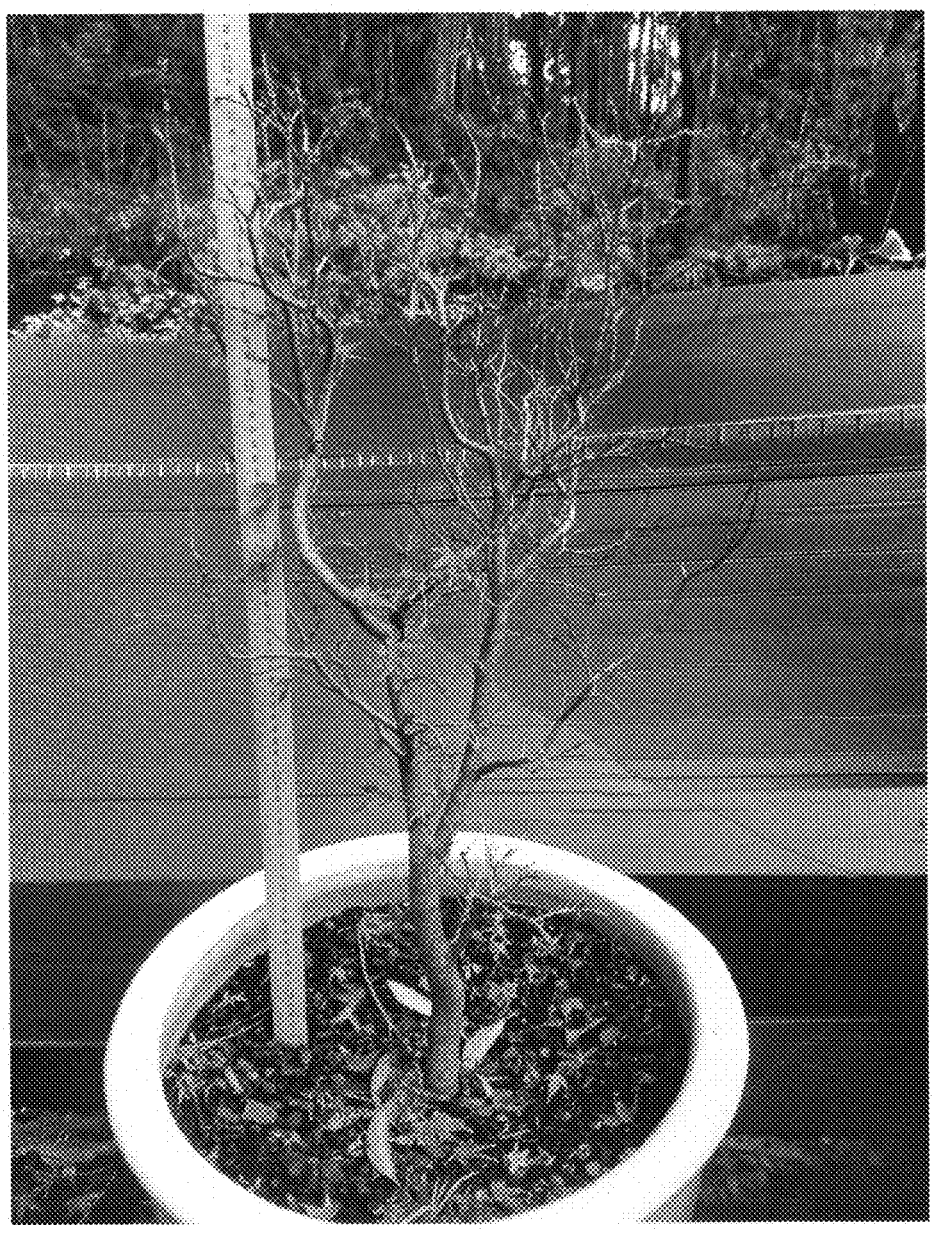

FIG. 2 illustrates the contorted branch pattern on a fully deciduous tree of the new variety. Age of the tree photographed in FIG. 2 is approximately 7 years.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'CHACER01' plants grown outdoors and in a nursery in Toolangi, Victoria, Australia (37° 30'36"S, 145° 27'52"E, 203 meters above sea level). Temperature ranged from approximately 12° C. to 25° C. during the day and from approximately 5° C. to 18° C. at night. Plants were measured during late Autumn. Age of the plants when described is approximately 3.5 years old. Measurements and numerical values represent averages of typical plant types.

Botanical classification: *Acer palmatum* 'CHACER01'.

PROPAGATION

Time to initiate roots: About 50 to 60 days at approximately 25° C.

Root description: Fibrous. Fine, brown roots not accurately measured with an R.H.S. chart.

PLANT

Growth habit: Upright, randomly branched dwarf tree.
Pot size of described plant: 15 cm pot.
Height: 50 to 60 cm.
Plant spread: 20 to 30 cm.
Branch internode length: 1 to 5 cm.
Branch characteristics:

*Length*.—Main branches are 25 to 30 cm.
*Diameter*.—0.2 to 0.5 cm.
*Texture*.—Mottled, slightly rough to smooth going into new season growth.
*Color*.—Near RHS Yellow-Green 148A, with reddish tinge on newer growth. Reddish tinge not accurately measured with R.H.S. chart.

Aspect and angle: Slight zigzag appearance angled from trunk of between 30 to 45° angle with secondary and tertiary laterals at irregular intervals also at 30 to 45° angles with laterals having the slight zigzag characteristic.

Trunk characteristics:

*Diameter*.—0.6 to 1.0 cm. Measured approximately 8 to 10 cm above soil level.
*Color*.—Near RHS Yellow-Green 148A.

Other branch and trunk characteristics:

*Lenticels present*.—Yes.
*Lenticel diameter*.—0.2 to 0.3 cm.
*Lenticel density*.—Moderate.
*Lenticel color*.—Near RHS White 155C.

FOLIAGE

Leaf:

*Arrangement*.—Opposite, rarely sub-opposite.
*Average length*.—Approximately 5.5 cm including petiole.
*Average width*.—Approximately 4.5 cm.
*Shape of blade*.—Palmately lobed. Lobe depth average 2.5 cm.
*Apex*.—Acuminate.
*Base*.—Obcordate.
*Margin*.—Doubly serrate.
*Texture of top surface*.—Smooth with raised veins.
*Texture of lower surface*.—Smooth with raised veins.
*Leaf internode length*.—Average range 1.0 to 2.0 cm.
*Typical leaf emergence day*.—Early September in Victoria, Australia.
*Typical leaf fall date*.—Mid-May in Victoria, Australia.
*Color*.—Young foliage: Upper side: Near RHS Yellow-Green 146C. Under side: Near RHS Yellow-Green 146D. Mature foliage: Upper side: Near RHS Green 137A. Under side: Near RHS Green 137C. Mature Fall foliage: Upper side: Near RHS Greyed-Red 179B. Under side: Near RHS Greyed-Orange 173C.

Foliage:

*Venation*.—Type: Palmate. Color: Venation color upper side: Near RHS Yellow-Green 144B. Venation color under side: Near RHS Yellow-Green 144B. Petiole: Length: Average 2.0 cm. Diameter: Average 0.1 cm. Color: Upper side: Near RHS Red-Purple 59B. Under side: Near RHS Yellow-Green 144B.

FLOWER

Flowering production not yet observed.

OTHER CHARACTERISTICS

Disease resistance: Tolerant to normal diseases.
Pest resistance: Unknown.

Drought resistance: Tolerant of drought conditions.

Temperature tolerance: Tolerant to high temperatures, to more than 40° C., determined in Toolangi, Australia. Cold temperature tolerance unknown.

What is claimed is:

1. A new and distinct cultivar of *Acer palmatum* tree named 'CHACER01' as herein illustrated and described.

* * * * *